United States Patent [19]

Mälson et al.

[11] Patent Number: 5,783,691
[45] Date of Patent: Jul. 21, 1998

[54] CROSSLINKED HYALURONATE GELS, THEIR USE AND METHOD FOR PRODUCING THEM

[75] Inventors: Tomas Mälson; Bengt Lindqvist, both of Uppsala, Sweden

[73] Assignee: Biomatrix, Inc., Ridgefield, N.J.

[21] Appl. No.: 638,322

[22] Filed: Apr. 26, 1996

Related U.S. Application Data

[63] Continuation of Ser. No. 357,131, Dec. 15, 1994, abandoned, which is a continuation of Ser. No. 217,074, Mar. 24, 1994, abandoned, which is a continuation of Ser. No. 921,012, Jul. 23, 1992, abandoned, which is a continuation of Ser. No. 572,955, Sep. 13, 1990, abandoned.

[30] Foreign Application Priority Data

Feb. 8, 1989 [JP] Japan ............................. 1-00422

[51] Int. Cl.$^6$ ................................................. C07H 5/04
[52] U.S. Cl. .................................. 536/55.1; 536/55.3
[58] Field of Search ............................. 536/55.1, 55.3

[56] References Cited

U.S. PATENT DOCUMENTS

| | | | |
|---|---|---|---|
| 3,422,088 | 1/1969 | Tuschhoff | 536/55.1 |
| 3,555,009 | 1/1971 | Suzuki | 536/123.12 |
| 3,936,441 | 2/1976 | Holst et al. | 536/44 |
| 4,152,170 | 5/1979 | Nagase | 106/205.1 |
| 4,605,691 | 8/1986 | Balazs et al. | 536/4.1 |
| 4,716,154 | 12/1987 | Malson et al. | 514/54 |
| 4,716,224 | 12/1987 | Sakurai et al. | 536/55.1 |
| 4,957,744 | 9/1990 | della Valle et al. | 424/401 |

FOREIGN PATENT DOCUMENTS 442820  3/1986  Sweden.

OTHER PUBLICATIONS

Balasz Chemical Abstracts vol. 98, No. 19, No 161088y, 1983.

*Primary Examiner*—Elli Peselev
*Attorney, Agent, or Firm*—Galvin & Palmer

[57] ABSTRACT

The present invention relates to a crosslinked hyaluronic acid derivative in which the crosslinking has been achieved by means of reaction with a phosphorus-containing reagent, especially a derivative of an acid of phosphorus (V). The invention also relates to the methods of producing such a product as well as its use as a slow release depot for administration of hyaluronic acid or a medicament incorporated in the gel.

14 Claims, No Drawings

CROSSLINKED HYALURONATE GELS, THEIR USE AND METHOD FOR PRODUCING THEM

This is a continuation of application Ser. No. 08/357,131 filed Dec. 15, 1994, which is continuation of application Ser. No. 08/217,074 filed Mar. 24, 1994, which is a continuation of application Ser. No. 07/921/012 filed Jul. 23, 1992, which is a continuation of application Ser. No. 07/572,955 filed Sep. 13, 1990 all four now abandoned Jul. 23, 1992.

The present invention relates to a crosslinked hyaluronic acid derivative in which the crosslinking has been achieved by means of reaction with a phosphorus-containing reagent, especially a derivative of an acid of phosphorus(V). The invention moreover also relates to methods for producing such a product as well as its use as a slow release depot for administration of hyaluronic acid or a medicament, incorporated in the gel.

Hyaluronic acid is a high molecular weight polysaccharide, highly viscous in character and consisting of a disaccharide repeating unit of N-acetylglucosamine and glucuronic acid. It occurs naturally in the body of humans and animals, for instance in synovial fluid, vitreous humor and pericardial fluid. In all species, the structure of hyaluronic acid is the same whereas its molecular weight may vary within wide ranges. Because of its bioresorbability and absence of toxicologic and immunologic effects hyaluronic acid has been found to be useful in medical contexts, e.g for the treatment of articular disorders adversely affecting articular motility, and as a surgical aid in connection with eye surgery and for preventing post-operative adhesions. In such cases hyaluronic acid has been employed in the form of a viscous aqueous solution. However, in many cases the duration is too short and mechanical stabilization too weak so that the desired therapeutic effect is not attained.

Improvements in these respects have been obtained by means of chemically crosslinking the hyaluronic acid to form insoluble gels. The preparation of such gels and their use as vitreous humor substitutes and in treating retinal detachment are described in for instance U.S. Pat. No. 4716154. Controllably degradable gels, to be used in the first place as adhesion-preventing materials, are described in PCT application WO86/00912. A feature which these hyaluronic acid gels have in common is that non-endogenous structures which are "alien" to the body are introduced into the material by way of the crosslinking procedure. This circumstance detracts from the efficacy of the basic concept of using an endogenous substance like hyaluronic acid as the matrix for the crosslinking, because the new material will actually contain structures that are "alien" to the body. As a result, the endogenous, non-toxic and non-immunogenic hyaluronic acid may undergo a change such that the crosslinked material is recognized as being "alien"—with consequential immunological and inflammatory reactions.

We have now surprisingly found a novel biologically degradable crosslinked hyaluronic acid gel derivative which is produced by means of reacting the hyaluronic acid with a phosphorus-containing reagent, especially a phosphorus(V) acid derivative, and which contains endogenous crosslinks, viz., phosphate esters. Phosphate esters occur ubiquitously in vivo. As examples may here be mentioned phospholipids, DNA and RNA.

In many other respects, too, the process for the production of the phosphate-crosslinked hyaluronate gels and their properties are superior to the manufacturing processes and properties of prior art crosslinked hyaluronic acid materials. The crosslinking reaction time is very short, and the substances require a minimum of purification because the reactive crosslinking reagents are rapidly hydrolyzed. The gels are degradable biologically, and the degradation time is variable within wide limits. In contrast to prior art crosslinked hyaluronate gels the present gels are completely re-swellable after complete desiccation.

Phosphate crosslinking of polysaccharides is a known method, primarily for the treatment of starch (see for example Koch H et al., Sttrke 34 (1982) 16). However, the derivatization of starch is a treatment of an insoluble material in a heterogeneous system. Phosphate crosslinking of hyaluronic acid too may be carried out heterogeneously on solid material, for instance in pyridine. But for obtaining a more reproducibly swelling gel material the reaction preferably chosen is one where hyaluronic acid is treated in a dissolved state with a crosslinking reagent. This treatment may be performed in an organic solvent in which the hyaluronic acid has been solubilized, e.g. by way of salt formation with a lipophilic cation. Surprisingly, however, we have found that clear, transparent gels are obtained if the reaction is carried out in an aqueous solution of hyaluronate. Carrying out the reaction in aqueous solution is preferable from a handling and purification point of view.

Crosslinking reagents employed are derivatives of phosphorus(V) acid, in particular halides, oxyhalides or anhydrides thereof. Examples of such crosslinking reagents are phosphorus pentachloride, phosphoryl chloride (phosphorus oxychloride) or the corresponding bromide or iodide, phosphorus pentoxide and trimetaphosphates.

The reaction is carried out in an alkaline medium. The coupling and the hydrolysis of the phosphorus acid derivatives result in the release of relatively large amounts of acid. Both the phosphate esters formed and the hyaluronic acid matrix are sensitive to acidic degradation. It is very important, therefore, that enough base is present already from the very start of the reaction, since it is not possible to make any additions to the viscous gelling system. At the same time, however, the pH of the initial solution must not be too high because the hyaluronic acid is sensitive to alkaline degradation. This means, in the case of crosslinking in an aqueous solution, that the pH should be one between 9 and 14 (but note that pH values in the upper part of this range can be used only if the alkaline hyaluronate solution is prepared in situ, with cooling) and that the system has a sufficient buffer capacity. Bases that may be employed will thus be metal hydroxides such as sodium and potassium hydroxides. But already at low concentrations of these hydroxides a high initial pH will be obtained, while at the same time the buffer capacity for acid neutralization will be low. For this reason other bases, of better buffer capacity, should be employed: for example nitrogen bases like alkylamines, especially those that are sterically hindered such as triethylamine, tributylamine and methylmorpholine. However, a preferred preparation for crosslinking in aqueous solution employs basic metal phosphates like trisodium phosphate or tripotassium phosphate. In the work-up procedure of these gels the by-products obtained will only be biologically tolerable phosphate salts, there being thus no need to further proceed to purification steps for removing rests of potentially toxic alkalis. If the reaction is carried out in an anhydrous medium it is also possible to employ bases that are weaker than those mentioned above, for example pyridine.

If the crosslinking reaction is carried out homogeneously in a solution of hyaluronic acid the concentration thereof may vary within a wide range of concentrations. A practically useful concentration range is 2–15% (by weight) of hyaluronic acid in the reaction mixture. Already concentrations as low as 1% will give rise to gel formation, but these gels are of a very liquescent consistency and not very worthwhile for technical purposes. There is no theoretical upper limit for the hyaluronic acid concentration to be employed in the crosslinking operation. A practical upper limit, however, is set due to the circumstance that already at moderate concentrations high molecular weight hyaluronic acid will form solutions which are very difficult to work with. Therefore, in the case of a hyaluronic acid having a molecular weight of say about $10^6$ the concentration should not exceed about 10%.

The molecular weight of the hyaluronic acid employed for the crosslinking may vary within a wide range from some thousands to several millions, for example from 20,000 to $5 \times 10^6$ depending an the concentration thereof and on the amount of crosslinking agent. However, a preferred molecular weight range is one between about 100,000 and $4 \times 10^6$.

In addition to hyaluronic acid or hyaluronates such as e.g. the sodium salt, other derivatives of hyaluronic acid may be crosslinked in accordance with this method, such as for instance a partially sulfated hyaluronic acid or esterified hyaluronic acid (see EP 265116). This of course applies also to hyaluronic acid that has been subjected to some other minor chemical modification such as described in e.g. U.S. Pat. No. 4713448.

The amount of crosslinking agent, too, may vary within a wide range depending on the molecular weight and concentration of the hyaluronic acid. In a preferred embodiment with an aqueous solution of hyaluronic acid and phosphoryl chloride as the crosslinking agent the amount of the latter may vary from 10 to 500% by weight based on the hyaluronic acid.

The crosslinking reaction may be carried out at room temperature or at a somewhat elevated temperature. However, the reaction at these temperatures is very fast; gel formation will occur already after a few minutes' reaction time at room temperature. For better control of the reaction one will therefor choose a lower temperature, for example within the range of from 0 to 10° C.

It should be noted, however, that in a preferred reaction system where hyaluronate is crosslinked in an aqueous solution most of the crosslinking reagents are not completely soluble; instead these reagents and the aqueous phase will form a two-phase system. It is important, therefore, that the contact area between the crosslinker phase and the hyaluronic aqueous phase be made as large as possible. We have found that the crosslinking is favored by the rheological properties of hyaluronic acid because stable suspensions or emulsions of the crosslinking reagent will form very easily. The stability of the two-phase system will also be promoted by lowered temperatures.

The gel material, after having been swollen and finely divided in a physiologically acceptable buffer, will be readily injectable. The gel can be heat-sterilized, for instance by autoclaving. Also, in addition to injectable crushed gel preparations other preparations in the form of shaped materials may be produced, like for instance films, tubes etc.

In contrast to what is the case with epoxy-crosslinked hyaluronate gels (Laurent T.C. et al. in Acta Chem. Scand. 18 (1964), 274–275) the present gels are capable of complete re-swelling after having been desiccated, for example by freeze-drying. From a manufacturing point of view this is a considerable advantage, for by storing a dry stable intermediate product one will avoid such degradation as would occur if the gel were stored while being swollen in a buffer having a pH greater than 7. Also, it is easy to alter the concentration and swelling medium of the final gel composition.

The phosphorus content in dried gels will vary from some hundredth percent up to one percent. As regards gels crosslinked in a homogeneous aqueous solution, the solids content in a completely swollen gel in aqueous solution varies between 0.1 and 10%. On the other hand the degree of swelling will be much lower in gels crosslinked in a nonhomogeneous system with an incompletely dissolved hyaluronic acid. Typically in a film thus produced the solids content will be 30%.

The gels have a maximum of stability at pH 5.75 but are degradable at biological pH (7.3). But as compared to the carboxylate-crosslinked hyaluronate gels—which, too, are degradable and which are described in patent application WO86/00912 - the phosphate-crosslinked gels possess much greater stability. It is thus possible by means of said phophate-crosslinking to obtain hyaluronate gels-having considerably longer and more variable degradation times as compared to older types of gels. Gels may now be produced with degradation times of from about one day to a couple of months. The patent application EP272300 also describes a method of extending the degradation time of hyaluronate gels by means of a combination of carboxylate ester and ether crosslinking. Those gels, however, cannot be prepared in an injectable form.

According to one aspect of the invention gels are produced which contain also other components, e.g. pharmaceuticals, this being achieved by adding the desired component to the gel either before or after the crosslinking thereof, to thus obtain for instance a slow-release effect.

In another aspect of the invention the gels are used for slow release of soluble hyaluronate in vivo. Beneficial effects of local administration of hyaluronic acid, for instance in joints, are well known from the literature. One of the problems encountered so far is that the hyaluronate, in spite of its high viscosity, is removed too quickly out of the administration area, by diffusion. The degradation products of the present gels are, as earlier mentioned, hyaluronic acid and harmless phosphates, making these gels, when implanted, excellent depots for slow-release of hyaluronic acid.

The invention thus relates to a method for crosslinking hyaluronic acid by means of subjecting a solution of hyaluronic acid or a derivative thereof to treatment with a phosphorus-containing reagent, especially a phosphorus(V) acid derivative. The processes contemplated here are in the first place those where an aqueous solution of the hyaluronic acid or a derivative thereof is reacted in alkaline conditions, preferably pH 9–14, with a phosphorus(V) acid derivative. Preferred phosphorus(V) acid derivatives are at present considered to be halides, oxyhalides or anhydrides, for example phosphorus pentachloride, phosphoryl chloride (phosphorus oxychloride) or the corresponding bromide or iodide, phosphorus pentoxide and trimetaphosphates.

Furthermore, the invention comprises hyaluronic acid gels containing phosphate ester crosslinks produced as stated above, and the use of such gels as preparations for the administration of medicines and as slow-release depots for administration of hyaluronic acid.

A number of examples will be set forth below for the purpose of illustrating the invention, without, however, limiting the scope thereof in any way.

Unless otherwise stated a high molecular weight sodium hyaluronate ($M_w$ $3 \times 10^6$) has been employed for preparing the gels.

The gels have been swelled, washed and autoclaved in isotonic Sorensen buffer pH 5.75 (100 ml $Na_2HPO_4$ (9.470 g/l), 900 ml $NaH_2PO_4.H_2O$ (9.208 g/l) and 5200 mg NaCl per liter of solution).

The degradation times of the gels have been measured by incubation at 37° C. in phosphate-buffered saline pH 7.3, complete dissolution of the gel being checked by means of filtration.

EXAMPLE 1

500 mg of sodium hyaluronate were weighed into a centrifuge tube of glass. 8.3 ml of saturated trisodium phosphate ($Na_3PO_4$) solution were added. The polysaccharide was allowed to swell in the phosphate solution overnight in a refrigerator.

The sample was stirred with a glass rod until complete dissolution of the hyaluronate had taken place. The 6% hyaluronate solution thus prepared has a pH of about 12.8%.

The solution was cooled in an ice bath to about +1° C. 167 μl of phosphoryl chloride ($POCl_3$) were added with vigorous stirring. After a few minutes of stirring the solution gelled. The sample was stirred during five minutes all in all, whereupon it was centrifuged until a homogeneous clear gel was obtained.

After a further ten minutes' reaction time the resultant gel, which had a neutral pH, was cut into thin slices. The slices were transferred to one liter of Sorensen buffer. The gel was washed for two days with shaking, the buffer being replaced three times during this period. The yield of swollen gel was 35 ml.

The gel was crushed by being forced through a fine-meshed steel wire net and was filled into syringes which were then autoclaved. The soft, slightly cohesive gel could easily be injected through a fine injection needle.

The non-autoclaved gel had a degradation time of 5 weeks whereas the autoclaved gel was degraded within 3–4 weeks. The phosphorus content of the dialyzed dried gel amounted to 0.081%. The solids content of the swollen gel was 1.4%.

EXAMPLE 2

300 mg of sodium hyaluronate were swelled in 15 ml of water overnight in a refrigerator. By means of stirring the hyaluronate was made to dissolve completely so as to form a 2% solution. To this were added 3.75 g of solid sodium phosphate ($Na_3PO_4.12H_2O$). After the salt had dissolved the solution was cooled in an ice bath, whereupon crosslinking was carried out with 400 μl $POCl_3$ as according to Ex. 1.

The gel thus formed was dialyzed against dist. water for two days; then the material was crushed and freeze-dried. The phosphorus content was 0.10%. The dried gel was allowed to swell in Sorensen buffer for three days, and was then autoclaved. The gel thus obtained was cohesive, homogeneous, entirely clear, fairly mobile. The degradation time of the autoclaved gel amounted to 4–5 days.

EXAMPLE 3

The experiment of Ex. 2 was repeated, but this time a 3% solution was prepared with 300 mg of hyaluronate in 10 ml of water, with 2.5 g of $Na_3PO_4 \times 12H_2O$ as the base. 250 μl of $POCl_3$ were employed as the crosslinking agent.

In this case the swollen gel had a solids content of 3.6%. The degradation time of the autoclaved gel was 10 days. The phosphorus content of the dried gel was 0.085%.

EXAMPLE 4

400 mg of sodium hyaluronate were dissolved in 3.3 ml of water to thus form a very thick 12% solution. The sample was cooled to about +10° C. whereupon 1 ml of triethylamine (which is water-soluble below +18° C.) was added, with mixing. The pH of the solution was about 13.5. The sample was subjected to further cooling, down to +1° C., and was crosslinked with 183 μl of $POCl_3$.

A rigid gel was obtained having a phosphorus content of 0.12%. In autoclaved state, the gel had a degradation time of 4 weeks.

EXAMPLE 5

5 ml of 6% hyaluronate solution in water were mixed with 1 ml of 4-methylmorpholine; the pH of the solution was about 11.2. The solution was crosslinked with 200 μl of $POCl_3$ as stated above.

A somewhat liquescent gel was obtained. The gel was autoclaved on having been swelled in Sorensen buffer of pH 5.0. The non-autoclaved gel had a degradation time of between 15 and 19 days while after autoclaving the degradation time was 10 days.

EXAMPLE 6

In this example, crosslinking was tested in aqueous solutions with various different concentrations of sodium hydroxide as the base.

To 2.75 g of cooled 10% hyaluronate solution were added varying amounts of sodium hydroxide solution whereupon crosslinking was effected with a predetermined amount of crosslinker, 100 μl $POCl_3$.

a. 100 μl 5 M NaOH. After the $POCl_3$ addition the solution became rapidly very acidic (pH about 2). Only a very small amount of water-insoluble gel was obtained.

b. 250 μl 5 M NaOH. This too resulted rapidly in the formation of a very acidic reaction solution. The gel obtained had a very liquescent consistency and could not be autoclaved without being degraded.

c. 500 μl 5 M NaOH. After crosslinking, a gel of rather firm consistency was obtained. In its fully swollen condition it had a hyaluronate content of 0.6%. However, autoclaving resulted in considerable degradation of the gel. The autoclaved sample had a degradation time of 4 days.

d. 1000 μl 5 M NaOH. The hyaluronate was rapidly degraded by the alkaline liquor so as to form a solution of low viscosity. Addition of the crosslinker did not result in gel formation.

These examples clearly show that adequate buffer control is required in the crosslinking system.

EXAMPLE 7

300 mg of sodium hyaluronate were dissolved in 3 ml of saturated $Na_3PO_4$ solution so as to form a 10% solution which was then crosslinked with 25 μl of $POCl_3$. A rigid gel was obtained which had a degradation time amounting to 14 days.

EXAMPLE 8

80 mg of acid-degraded sodium hyaluronate having a molecular weight of 100,000 were dissolved in 1 ml of saturated $Na_3PO_4$ solution. To this was added a further 0.2 g of solid $Na_3 PO_4.12H_2O$. The solution was crosslinked with 75 μl $POCl_3$.

An opalescent brittle gel having a degradation time of two weeks was obtained.

EXAMPLE 9

300 mg of sodium hyaluronate were dissolved in 5 ml of saturated $Na_3PO_4$ solution. To the cooled solution 200 mg of phosphorus pentachloride (PCl$_5$) were added in small aliquots and with vigorous stirring. The phosphorus pentachloride reacted more rapidly and more violently than phosphoryl chloride. A somewhat opalescent gel was obtained which had a degradation time of two weeks.

EXAMPLE 10

200 mg of tetrabutyl ammonium hyaluronate were dissolved in 2 ml of dimethylformamide. This solution was admixed with 1 ml of triethylamine, whereupon the solution was cooled and 100 µl of POCl$_3$ were added. Gel formation was almost instantaneous. The gel that had been formed consisted of white flakes showing very little tendency of swelling in water. The gel had a hyaluronate content amounting to 30%.

EXAMPLE 11

100 mg of tetrabutyl ammonium hyaluronate were dissolved in 2 ml dimethylformamide. 200 µl of triethylamine were added, and the solution was cooled and admixed with 200 mg of diphosphorus pentoxide (P$_2$O$_5$). Almost immediately a white gel precipitate was formed, having the same properties as the gel prepared according to Ex. 10.

EXAMPLE 12

100 mg of sodium hyaluronate were evaporated with 3×10 ml dry pyridine. The substance was suspended in 10 ml of pyridine, whereupon the suspension was cooled and 400 µl of POCl$_3$ were added. The solution was shaken for 15 minutes. The hyaluronate thus treated, which is insoluble in water, will be liable to irregular swelling to thus form a mixture of hard white portions and clear gel portions. The hardest crosslinked white gel portions are not degradable at a physiological pH but will dissolve when subjected to alkaline treatment. The phosphorus content in the dialyzed dried gel was 0.77%.

EXAMPLE 13

Dialyzed salt-free sodium hyaluronate was dried in a petri dish so as to form a clear, planar film. The film was allowed to swell for some seconds in a cooled mixture of one part of water and nine parts of triethylamine. The swollen film was treated with phosphoryl chloride, either by being dipped into it for some seconds or by being maintained in phosphoryl chloride vapor during about one minute. In both cases a clear, water-insoluble crosslinked film was obtained; in its swollen state it had a solids content of about 30%.

We claim:

1. A process for preparing gels of crosslinked sodium hyaluronate which comprises reacting a solution of the sodium hyaluronate with a phosphorus (V) acid derivative selected from the group consisting of a phosphorus (V) acid halide, a phosphorus (V) acid oxyhalide and a phosphorus (V) acid anhydride under crosslinking conditions.

2. A process according to claim 1 wherein the phosphorus (V) acid derivative is phosphoryl chloride.

3. A process according to claim 1 wherein the phosphorus (V) acid derivative is phosphorus (V) acid oxyhalide.

4. A process according to claim 1 wherein the phosphorus (V) acid derivative is phosphorus pentoxide.

5. A process according to claim 1 wherein the phosphorus (V) acid derivative is phosphorus pentachloride.

6. A process according to claim 1 wherein the phosphorus (V) acid derivative is diphosphorus pentoxide.

7. A process for preparing gels of crosslinked hyaluronic acid or derivatives thereof which comprises reacting a solution of the hyaluronic acid or a derivative thereof with a phosphorus (V) acid derivative selected from the group consisting of a phosphorus (V) acid halide, a phosphorus (V) acid oxyhalide and a phosphorus (V) acid anhydride under crosslinking conditions.

8. A process according to claim 7 wherein the phosphorus (V) acid derivative is phosphoryl chloride.

9. A process according to claim 7 wherein the phosphorus (V) acid derivative is phosphorus (V) acid oxyhalide.

10. A process according to claim 7 wherein the phosphorus (V) acid derivative is phosphorus pentoxide.

11. A process according to claim 7 wherein the phosphorus (V) acid derivative is phosphorus pentachloride.

12. A process according to claim 7 wherein the phosphorus (V) acid derivative is diphosphorus pentoxide.

13. A gel of crosslinked hyaluronic acid or a derivative thereof wherein the crosslinks are phosphate ester bridges.

14. A gel produced according to the process of claim 1.

* * * * *